(12) United States Patent
Liao et al.

(10) Patent No.: US 7,371,574 B2
(45) Date of Patent: May 13, 2008

(54) ANTIBODY ANTAGONISTS OF VE-CADHERIN WITHOUT ADVERSE EFFECTS ON VASCULAR PERMEABILITY

(75) Inventors: Fang Liao, New York, NY (US); Daniel J. Hicklin, Glen Ridge, NJ (US); Peter Bohlen, New York, NY (US)

(73) Assignee: Imclone Systems, Inc., New York, NY (US)

( * ) Notice: Subject to any disclaimer, the term of this patent is extended or adjusted under 35 U.S.C. 154(b) by 606 days.

(21) Appl. No.: 10/040,128

(22) Filed: Jan. 2, 2002

(65) Prior Publication Data

US 2002/0160003 A1   Oct. 31, 2002

Related U.S. Application Data

(63) Continuation of application No. 09/540,967, filed on Mar. 31, 2000, now abandoned.

(51) Int. Cl.
*C12N 5/20* (2006.01)
(52) U.S. Cl. .................. 435/334; 530/350; 530/388.22
(58) Field of Classification Search ............ 530/387.1, 530/387.9, 388.1, 300, 350, 388.22, 387.7, 530/388.8, 389.1, 389.7; 435/326, 334; 424/130.1
See application file for complete search history.

(56) References Cited

U.S. PATENT DOCUMENTS

| | | | |
|---|---|---|---|
| 5,597,725 A | 1/1997 | Suzuki | |
| 5,646,250 A * | 7/1997 | Suzuki | .................. 530/350 |
| 2003/0206902 A1 * | 11/2003 | Liao et al. | ............... 424/143.1 |
| 2005/0222037 A1 * | 10/2005 | Blaschuk et al. | ............ 514/14 |

FOREIGN PATENT DOCUMENTS

WO   WO 99/57149 A2 * 11/1999

OTHER PUBLICATIONS

Corada et al. Blood, vol. 97, No. 6, Mar. 2001.*
Greenspan et al. Nature Biotechnology 7:936-937 1999.*
Database IMSDRUGNEWS (R & D Focus Drug News, Nov. 17, 1997).*
Skolnick et al. (Trends Biotechnol. 2000; 18 (1): 34-39).*
Bowie et al. (Science 1990; 257: 1306-1310).*
Burgess et al. (Journal of Cell Biology 1990; 111: 2129-2138).*
Lazar et al. (Molecular and Cellular Biology, 1988, 8: 1247-1252).*
Luque et al. (Biochem. Nov. 19, 2002; 41 (46): 13663-13671).*
Vucic et al. (J. Biol. Chem. Dec. 18, 1998; 273 (51): 33915-33921).*
Takada et al. (Mol. Endocrinol. 2000; 14 (5): 733-740).*
Guo et al. (Proc. Natl. Acad. Sci. USA. Jun. 22, 2004; 101 (25): 9205-9210).*
Gura (Science. 1997; 278: 1041-1042).*
Saijo et al. (Cancer Sci. Oct. 2004; 95 (10): 772-776).*
Kelland (Eur. J. Cancer. Apr. 2004; 40 (6): 827-836).*
Schuh (Toxicologic Pathology. 2004; 32 (Suppl. 1): 53-66).*
Bibby (Eur. J. Cancer. Apr. 2004; 40 (6): 852-857).*
Peterson et al. (Eur. J. Cancer. 2004; 40: 837-844).*
Dennis (Nature. Aug. 7, 2006; 442: 739-741).*
Navarro et al. (J. Cell Biol. Mar. 23, 1998; 140 (6): 1475-1484).*
Lampugnani et al. (J. Cell. Biol. 1992; 118: 1511-1522).*
Yang et al. (Am. J. Pathol. Sep. 1999; 155 (3): 887-895).*
Bach et al. (J. Biol. Chem. Nov. 13, 1998; 273 (46): 30719-30728).*
May et al. (Blood. Jun. 1, 2005; 105 (11): 4337-4344).*
Liao et al. (Cancer Res. Dec. 15, 2000; 60: 6805-6810).*
Corada et al. (Blood. Aug. 1, 2002; 100 (3): 905-911).*
Carmeliet et al., "Targeted Deficiency or Cytosolic Truncation of the VE-cadherin Gene in Mice Impairs VEGF-Mediated Endothelial Survival and Angiogenesis," Cell, vol. 98, Jul. 23, 1999, pp. 147-157.
Vittet et al., "Targeted Null-mutation in the Vascular Endothelial-Cadherin Gene Impairs the Organization of Vascular-like Structures in Embryoid Bodies," Proc. Natl. Acad. Sci. USA, vol. 94, Jun. 1997, pp. 6273-6278.
Caveda et al., "Inhibition of Cultured Cell Growth by Vascular Endothelial Cadherin (Cadherin-5/VE-Cadherin)," J. Clin. Invest., vol. 98, No. 4, Aug. 1996, pp. 886-893.
Corada et al., "Vascular Endothelial-cadherin is an Important Determinant of Microvascular Integrity In Vivo," Proc. Natl. Acad. Sci. USA, vol. 96, Aug. 1999, pp. 9815-9820.
Uemura et al., "The Cadherin Superfamily at the Synapse: More Members, More Missions," Cell, vol. 93, Jun. 26, 1998, pp. 1095-1098.
Bach et al., "VE-Cadherin Mediates Endothelial Cell Capillary Tube Formation in Fibrin and Collagen Gels," Experimental Cell Research, vol. 238, No. 2, 1998, pp. 324-334.
Breier et al., "Molecular Cloning and Expression of Murine Vascular Endothelial-Cadherin in Early Stage Development of Cardiovascular System," Blood, vol. 87, No. 2, Jan. 15, 1996, pp. 630-641.
Maschio et al., "Polymorphonuclear Leukocyte Adhesion Triggers the Disorganization of Endothelial Cell-to-Cell Adherens Junctions," The Journal of Cell Biology, vol. 135, No. 2, Oct. 1996, pp. 497-510.
Martin-Padura et al., "Functional Adhesion Molecule, a Novel Member of the Immunoglobulin Superfamily that Distributes at Intercellular Junctions and Modulates Monocyte Transmigration," The Journal of Cell Biology, vol. 142, No. 1, Jul. 13, 1998, pp. 117-127.
Liao et al., "Identification of antibody-based VE-cadherin antagonists for the application of anti-angiogenesis therapy," Proc. Nat'l Acad. Sci. USA, vol. 41, Mar. 2000, abstract #4096.

(Continued)

*Primary Examiner*—Stephen L. Rawlings
(74) *Attorney, Agent, or Firm*—Lucas & Mercanti, LLP

(57) ABSTRACT

The murine epitope sequence recognized by antibody E4B9 shares 100% homology with human VE-cadherin, so this antibody was examined to determine if it cross-reacts with human VIE-cadherin. Western-blot analysis of several VE-cadherin expressing human and murine ceH indicated that E4B9 indeed cross-reacts with human VE-cadherin (FIG. 6). This finding facilitates development of a "humanized" E4B9 antibody and its success in the prectinical development since its anti-tumor activity can be tested extensively in several mouse models.

11 Claims, 9 Drawing Sheets

OTHER PUBLICATIONS

Breviario et al., "Functional properties of human vascular endothelial cadherin (7B4/cadherin-5), and endothelium-specific cadherin," Arteriosclerosis, Thrombosis, and Vascular Biology, vol. 15, No. 8, Aug. 1995, pp. 1229-1239.

Haselton et al., "Role of cadherins 5 and 13 in the aortic endothelial barrier," Journal of Cellular Physiology, vol. 171, No. 3, Jun. 1997, pp. 243-251.

Corada et al., "Monoclonal antibodies directed to different regions of vascular endothelial cadherin extracellular domain affect adhesion and clustering of the protein and modulate endothelial permeability," Blood, vol. 97, No. 6, Mar. 15, 2001, pp. 1679-1684.

Takeichi, Ann. Rev. Biochem. (1990), 59:237-252.

Geiger & Ayalon, Ann. Rev. Cell Biol. (1992), 8:302-332.

Nose et al., Cell (1988), 54:993-1001.

Shapiro et al., Nature (1996), 374:327-337.

Lampugnani et al., J. Cell. Biol. (1992), 118:1511-1522.

Rabiet et al., Arterioscler. Thromb. Vasc. Biol. (1996), 16:488-496.

Dejana, J. Clin. Invest. (1997), 100:S7-10.

Dejana et al., Faseb J. (1995), 9:910-918.

Dejana et al., Ann NY Acad Sci. (1997), 811:36-43.

Kevil et al., J. Biol. Chem. (1988) 273:15099-15103.

Yap et al., J. Cell Biol. (1998), 141:779-789.

Faure et al., Development (1999), 128: 2093-2101.

Ali et al., Microcirculation 4:267-277 (1997).

Berman et al., EMBO J. 7:727-738 (1988).

Bowie et al., Science, 247:1306-1310 (1990).

Burgess et al., J. of Cell Bio. 111:2129-2138 (1990).

Cole, et al., 1985, In Moloclonal Antibodies and Cancer therapy, Alan R. Liss, Inc., pp. 77-96.

Gillman & Smith, Gene 8:81-97 (1979).

Gotsch et al., J. Cell Sci. 110:583-588 (1997).

Gumbiner, B., & Simons, K., Cell Biol. 102:457-468 (1996).

Kohler & Milstein, Nature, 256:495-497 (1975).

Kozbor et al., Immunology Today 4:72, (1983).

Lampugnani et al., J. Cell Biol. 129:203-217 (1995).

Lazar et al., Molecular and Cellular Biology 8:1247-1252 (1988).

Nagar et al., Nature 380:360-364 (1996).

Overduin et al., Science 267:386-389 (1995).

Queen, Nature 351:501 (1991).

Roberts, et al., Nature 328:731-734 (1987).

Piggot et al. (1991) Structural and Functional Studies of the Endothelial Activation Antigen Endothelial Leucocyte Adhesion Molecule-1 . . . , J. Immun. 147(1): 130-135.

* cited by examiner

```
DWVIPPINLPENSRGPFPQELVRIRSDRDKNLSLRYSVTGPGADQPPTGIFIINP              mNC (SEQ ID NO: 7)
DWVIPPISCPENEKGEFPKNLVQIKSNRDKETKVFYSITGQGADKPPVGVFIIER              mEC (SEQ ID NO: 8)
            4.8G                       BV9           Cad5
DWIWNQMHIDEEKNTESPHHVGKIKSSVSRK-NAKYLLKGEYVGK----VERVDA              hVEC (SEQ ID NO: 9)
DWIWNQMHIDEEKNESLPHYV-KDQSNVNRQ-NAKYVLQEFAGK----IFGVDA        mVEC (SEQ ID NO: 10)
        Peptide 1                 Peptide 2         Peptide 3

ISGQLSVTKPLDRELIARFHLRAHAVDIN-GNQVENPIDIVINVIDMNDNRPEF               mNC (SEQ ID NO: 11)
ETGWLKVTQPLDREAIAKYILYSHAVSSN-GEAVEDPMEIVITVTDQNDNRPEF               mEC (SEQ ID NO: 12)
ETGDVFAIERLDRENISEYHLTAVIVDKDTGENLETPSSFTIKVHDVNDNWPVE           hVEC (SEQ ID NO: 13)
NTGNVLAYERLDREKVSEYFLTALIVDKNTNKNLEQPSSFTVKVHDINDNWPVF           mVEC (SEQ ID NO: 14)
                                   Peptide 4
```

FIG. 2

DWIWNQMHIDEEKNESLPHYVKDQSNVNRQNAKYVLQGEFAGKIFGVDAN (SEQ ID NO: 15)
   E4B9                                        19E6,10G4(Cad5)

TGNVLAYERLDREKVSEYFLTALIVDKNTNKNLEQPSSFTVKVHDINDNWPVF (SEQ ID NO: 16)

Murine ECD1

ANTIBODY ANTAGONISTS OF VE-CADHERIN WITHOUT ADVERSE EFFECTS ON VASCULAR PERMEABILITY

CROSS-REFERENCE TO RELATED APPLICATIONS

The present application is a continuation of U.S. application Ser. No. 09/540,967, filed Mar. 31, 2000, now abandoned.

FIELD OF THE INVENTION

The present invention relates to antibody antagonists of VE-cadherin that inhibit formation new of adherens junctions without disrupting the integrity of existing junctions. Such antibodies are useful to prevent angiogenesis in a variety of disease conditions, including, for example, to prevent neovascularization of tumors. These antibodies are also useful for treating endothelial cell proliferative disorders.

BACKGROUND OF THE INVENTION

Many diseases are associated with an abnormal proliferation of blood vessels. The process of forming new blood vessels is termed angiogenesis. Under normal or non-pathologic conditions angiogenesis occurs under well-defined conditions such as in wound healing, in response to ischemia and during embryonal and fetal development. However, persistent or uncontrolled angiogenesis can lead to a variety of disease states or conditions and, in the case of solid tumors, may be a necessary condition to maintain the disease state. For example, angiogenesis occurs with neoplastic diseases, particularly with solid tumors, in autoimmune diseases, in collagenous vascular diseases such as rheumatoid arthritis, and in certain ophthalmalogical conditions such as diabetic retinopathy, retrolental fibroplasia and neovascular glaucoma. One therapeutic approach for the treatment of such diseases would be to restrict, reduce or eliminate the blood supply to the diseased cells or tissues. For example, solid tumors greater than a few millimeters undergo neovascularization without which further tumor growth would be impossible, so that inhibiting blood vessel formation will limit tumor size.

Some treatment strategies have attempted to limit the tumor's blood supply by occluding blood vessels supplying the tumor. For such treatment, the site of the tumor must be known and the tumor must be accessible. Thus a method of treatment that did not rely on knowing the location of or the accessibility to the site of interest would be valuable and could permit systemic delivery of a therapeutic anti-angiogenesis agent capable of specifically targeting a disease site.

Because of the role that angiogenesis plays in the development of disease, there is substantial interest in the development of angiogenesis inhibitors, especially where current therapies are less than optimal. Since endothelial cells are an integral part of blood vessel formation, a specific inhibitor of such cells would be advantageous in inhibiting angiogenesis, provided, of course, there is a minimum toxicity associated with that inhibitor. One particular target of interest is the endothelial cell-specific cadherin, VE-cadherin, that forms intercellular adherens junctions.

Cadherins are a family of cell adhesion molecules that are involved in the formation of specific cell-cell contacts (Takeichi, *Ann. Rev. Biochem.* 59: 237-252 (1990); Geiger & Ayalon, *Ann. Rev. Cell Biol.* 8: 302-332 (1992); Uemura, *Cell* 93: 1095-1098 (1998)). A number of members have been identified or characterized. Cadherins are single chain transmembrane glycoproteins with molecular weights of 120-140 kD. Members of this family exhibit calcium-dependent homophilic interactions and are responsible for the selective cell-cell recognition and adhesion, which is necessary for allocating different cell types to their proper places during organ development. Cadherins also play an important role in maintaining the integrity of multicellular structures. During embryonic morphogenesis the expression of diverse members of the cadherin family is spatially and temporally regulated facilitating the orderly assembly of various cell types into functional structures (Takeichi, *Ann. Rev. Biochem.* 59: 237-252 (1990)).

Members of the cadherins family have typical structural features and share considerable sequence homology (43-58%). Their extracellular region typically contains 5 repeating domains of approximately 110 amino acids. The N-terminal domain has been shown to be important in homotypic cell-cell interaction as evidenced by experiments with molecular chimeras, monoclonal antibodies and peptide inhibitors (Nose et al., *Cell* 54: 993-1001 (1988)). The 3-dimensional structures of the N-terminal domains of N-cadherin and E-cadherin have been elucidated (Shapiro et al., *Nature* 374: 327-337 (1995); Overduin et al., *Science* 267: 386-389 (1995); Nagar et al., *Nature* 380: 360-364 (1996)). Accordingly, it is believed that cadherins form dimers supported by zipper-like elements and possibly by disulfide linkage. The short intracellular portion of cadherins is their most highly conserved region and plays an essential role in classic cadherin function by anchoring cadherins to the cytoskeleton and providing signaling functions through cadherin phosphorylation (See, FIG. 1).

VE-cadherin (or cadherin-5) has been shown to be localized at intercellular junctions (adherens junctions) in cell-to-cell contacts (Lampugnani et al., *J. Cell. Biol.* 118: 1511-1522 (1992); Breviario et al., *Arterioscler. Thromb. Vasc. Biol.* 15: 1229-1239 (1995); Breier et al., *Blood* 87: 630-641 (1996); Lampugnani et al., *J. Cell Biol.* 129: 203-217 (1995)). A number of experimental observations suggest that this cadherin is involved in various aspects of vascular biology related to angiogenesis, including the assembly of endothelial cells into tubular structures (Bach et al., *Experimental Cell Research* 238: 324-334 (1998)). For example, thrombin-induced vascular permeability is shown to be associated with disassembly of endothelial adherens junctions (Rabiet et al., *Arterioscler. Thromb. Vasc. Biol.* 16: 488-496 (1996); Dejana, *J. Clin Invest.* 100: S7-10. (1997); Dejana et al., *FASEB J.,* 9: 910-918 (1995); Dejana et al., *Ann N Y Acad Sci.* 811: 36-43 (1997); Gotsch et al., *J. Cell. Sci.* 110: 583-588 (1997); Kevil et al., *J. Biol. Chem.* 273: 15099-15103 (1998); Corada et al., *Proc. Natl. Acad. Sci.* 96: 9815-9820 (1999)). VE-cadherin and its N-terminal fragment inhibit the density-dependent growth (Yap et al., *J. Cell Biol.* 141: 779-789 (1998); Caveda et al., *J. Clin. Invest.* 98: 886-893 (1996)) and migration (Breviario et al., *Arterioscler. Thromb. Vasc. Biol.* 15: 1229-1239 (1995)) of endothelial cells. In other experiments, VE-cadherin was shown to confer adhesive properties to transfected cells (Breviario et al., *Arterioscler. Thromb. Vasc. Biol.* 15: 1229-1239 (1995); Breier et al., *Blood* 87: 630-641 (1996); Ali et al., *Microcirculation* 4: 267-277 (1997)), and an essential role for VE-cadherin in blood vessel formation has been demonstrated in VE-cadherin null mice. In these mice, severely impaired assembly of vascular structures leads to an embryonic lethal phenotype (Vittet et al., *Proc. Natl. Acad. Sci.* 94: 6273-6278 (1997); Faure et al., *Development*

128: 2093-2102 (1999); Carmeliet et al., *Cell* 98: 147-157 (1999)). These findings strongly validate VE-cadherin as an attractive pharmacological target for inhibiting neovascularization.

Prior to the present invention, attempts to use VE-cadherin antibody antagonists to prevent angiogenesis have been limited by the toxicity of the antibody to normal vasculature. For example, administering certain anti-cadherin antibodies in amounts sufficient to prevent or inhibit angiogenesis have resulted in disturbances in the integrity of normal vasculature with resultant vascular leak syndromes, hemorrhage and death. For example, the anti-VE-cadherin antibody 19E6 results in increased pulmonary vascular permeability because that antibody disrupts existing VE-cadherin-mediated cellular junctions as well as preventing formation of new VE-cadherin-mediated cellular adherens junctions. The present invention addresses now provides improved VE-cadherin antibody antagonists directed to particular sites on VE-cadherin and which overcome such problems.

SUMMARY OF THE INVENTION

The present invention is directed to an antibody or an antibody fragment that is an antagonist of VE-cadherin. The antibody and antibody fragments of the invention are capable of specifically binding to a molecule selected from the group consisting of a site on a VE-cadherin, said site being within the about 15 to about 20 N-terminal amino acids of domain 1 of a VE-cadherin, a site on a VE-cadherin, said site being within the about 15 to about 20 N-terminal amino acids of domain 1 of a VE-cadherin and said N-terminal amino acids having an insertion, deletion or substitution of from 1 to about 5 amino acids relative to a native VE-cadherin amino acid sequence, a peptide having an amino acid sequence of SEQ ID NO: 1

(DEIWNQMHIDEEKNE), a peptide having an amino acid sequence of SEQ ID NO: 2

(DWIWNOMHIDEEKNE), and a peptide having an amino acid sequence of SEQ ID NO: 3

(DWIWNOMHIDEEKNT). Furthermore, the antibody or antibody fragment of the invention is capable of inhibiting VE-cadherin mediated adherens junction formation in vitro but does not exert any significant or substantial effect on paracellular permeability in vitro. Such antibodies and antibody fragments do not exert any significant or substantial effect on vascular permeability in vivo and are substantially non-toxic when administered to an animal or mammal. In addition, the antibodies or antibody fragments are capable of inhibiting angiogenesis in vivo or in vitro as well as tumor metastasis. The antibodies and antibody fragments of the invention act by inhibiting formation of new adherens junctions without disturbing existing adherens junctions. Preferred antibodies of the invention are monoclonal antibodies. Likewise, preferred antibody fragments are from monoclonal antibodies. In a more preferred embodiment, the monoclonal antibody is monoclonal antibody E4B9. The preferred mammal of the invention is a human.

The antibodies and or antibody fragment of the instant invention can be a single chain antibody, humanized, chimerized, bispecific, or fused to a heterologous polypeptide.

Another aspect of the invention is directed to a hybridoma which produces the monoclonal antibodies of the invention.

A further aspect of the invention provides pharmaceutical compositions comprising the antibody or antibody fragment of the invention in admixture with a pharmaceutically acceptable carrier or diluent.

Yet another aspect of the invention relates to a method of inhibiting angiogenesis in a mammal by administering the pharmaceutical composition of the invention to a mammal for a time and in an amount effective to inhibit angiogenesis.

Still another aspect of the invention is directed to a method of inhibiting tumor metastasis in a mammal by administering the pharmaceutical composition of the invention to a mammal for a time and in an amount effective to inhibit metastasis of a tumor.

Further still, the invention includes a method of treating a cell proliferative disorder associated with vascularization in a mammal by administering a pharmaceutical composition of the invention to a mammal in an amount effective to inhibit proliferation of endothelial cells without disturbing the normal vasculature. Cell proliferative disorder, include but are not limited to, blood vessel proliferative disorders, fibrotic disorders, angiogenesis, tumor growth, tumor metastasis, rheumatoid arthritis, and age-related muscular degeneration.

Yet another embodiment of the invention provides a method for reducing or inhibiting tumor vasculature in a mammal by administering a pharmaceutical composition of the invention to a mammal in an amount effective to inhibit blood vessel formation without adversely affecting existing vasculature, i.e., so to eliminate or substantially reduce or restrict blood flow to a tumor without adversely affecting existing vasculature.

The invention also provides an isolated nucleic acid comprising a nucleotide sequence which encodes a coding sequence for the antibody or antibody fragment, for a variable region of said antibody or for a hypervariable region of said antibody in accordance with the invention.

In yet a still further embodiment the present invention is directed to a method of gene therapy to deliver the antibody or antibody fragment of the invention to a mammalian host. This method is comprises administering a nucleic acid encoding the desired antibody or antibody fragment to a mammal in an amount and for a time effective to inhibit angiogenesis at a predetermined site or to inhibit tumor neovascularization.

BRIEF DESCRIPTION OF THE FIGURES

FIG. 2: Sequence Alignment of ECD1 of Four Classic Cadherins. Four regions of domain 1 for VE-cadherin are predicted to encompass the binding surface of either the strand dimer or the adhesion dimer. Four peptides (lower panels) are synthesized that encompass these regions to generate specific antibody inhibitors. Peptides 1: DEIWN-QMHIDEEKNE-Cys; 2: YVKDQSNYNRQNAKY-Cys; 3: KYVLQGEFAGKIFGVDA-Cys and 4: LIVDKNTNKN-LEQP-Cys. These peptides are represented by SEQ ID NOS.

1 and 4-6, respectively. The cysteine residue was added at the carboxyl end of each peptide for KLH-coupling.

Figure 1:
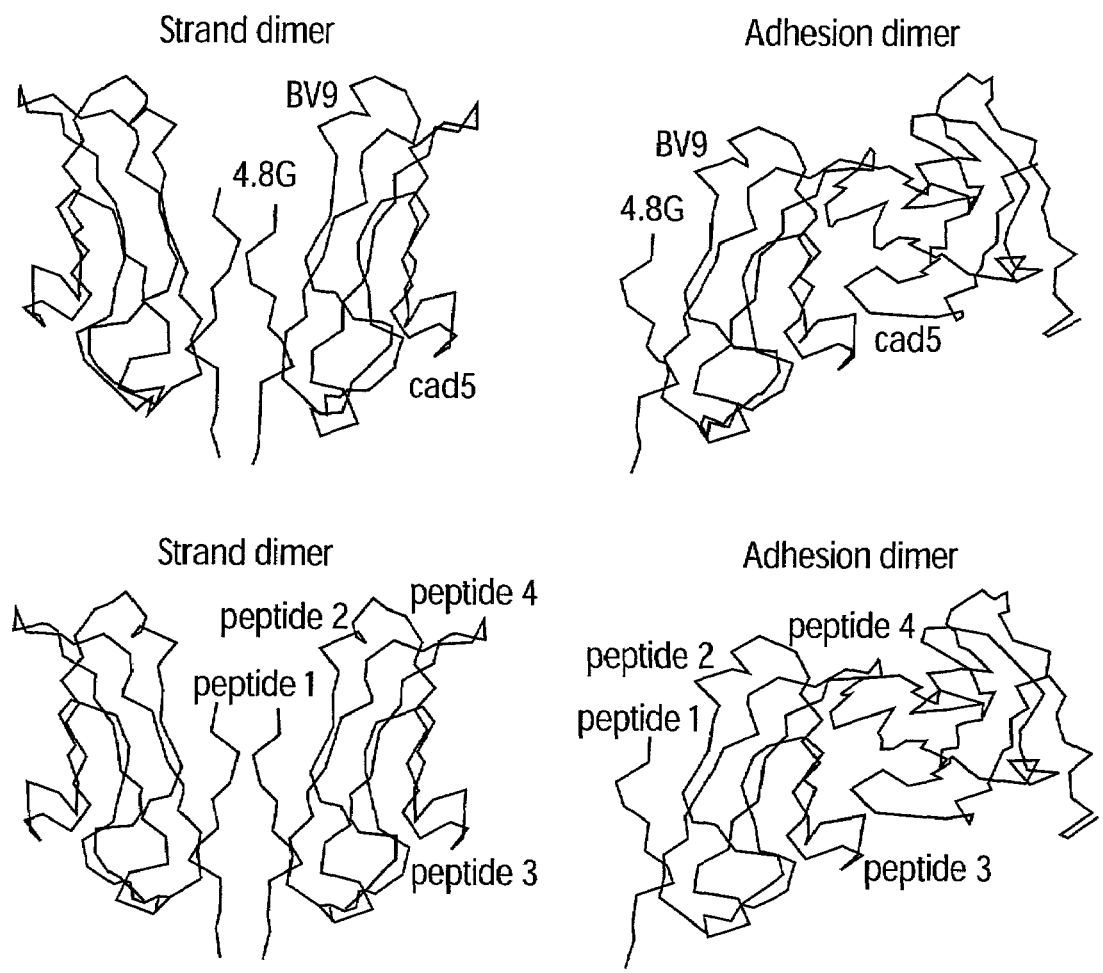
FIG. 1: VE-cadherin Dimerization. Two forms of VE-cadherin dimers are proposed based on the crystal structures resolved for N-and E-cadherins. The "strand dimer" (left panels) refers to homophilic interactions between two VE-cadherin molecules on the surface of the same cell. The "adhesion dimer" (right panels) refers to homophilic interactions between VE-cadherin molecules located on opposing cells.
Figure 3:
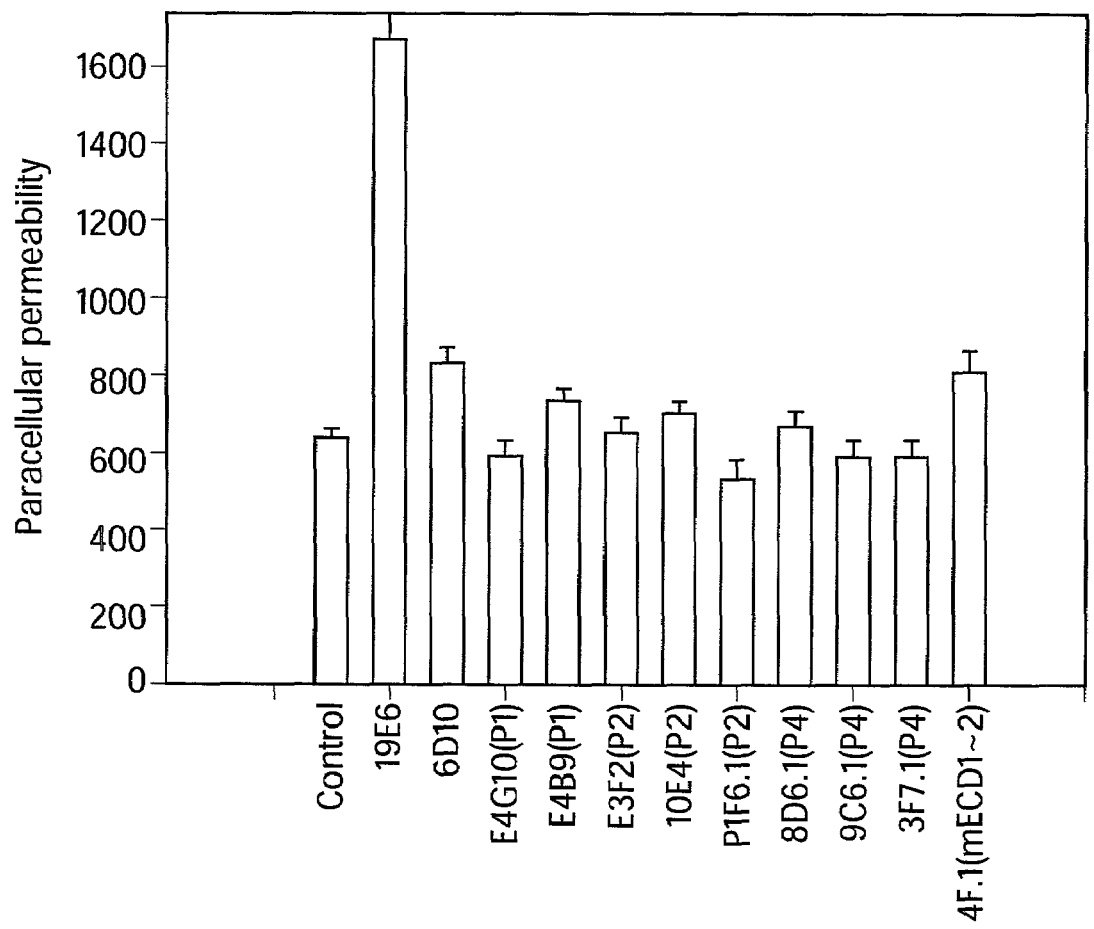

FIG. 3:. Effects of the anti-ECD1 (extracellular domain) peptides antibodies on paracellular permeability of H5V cells.

Figure 4:
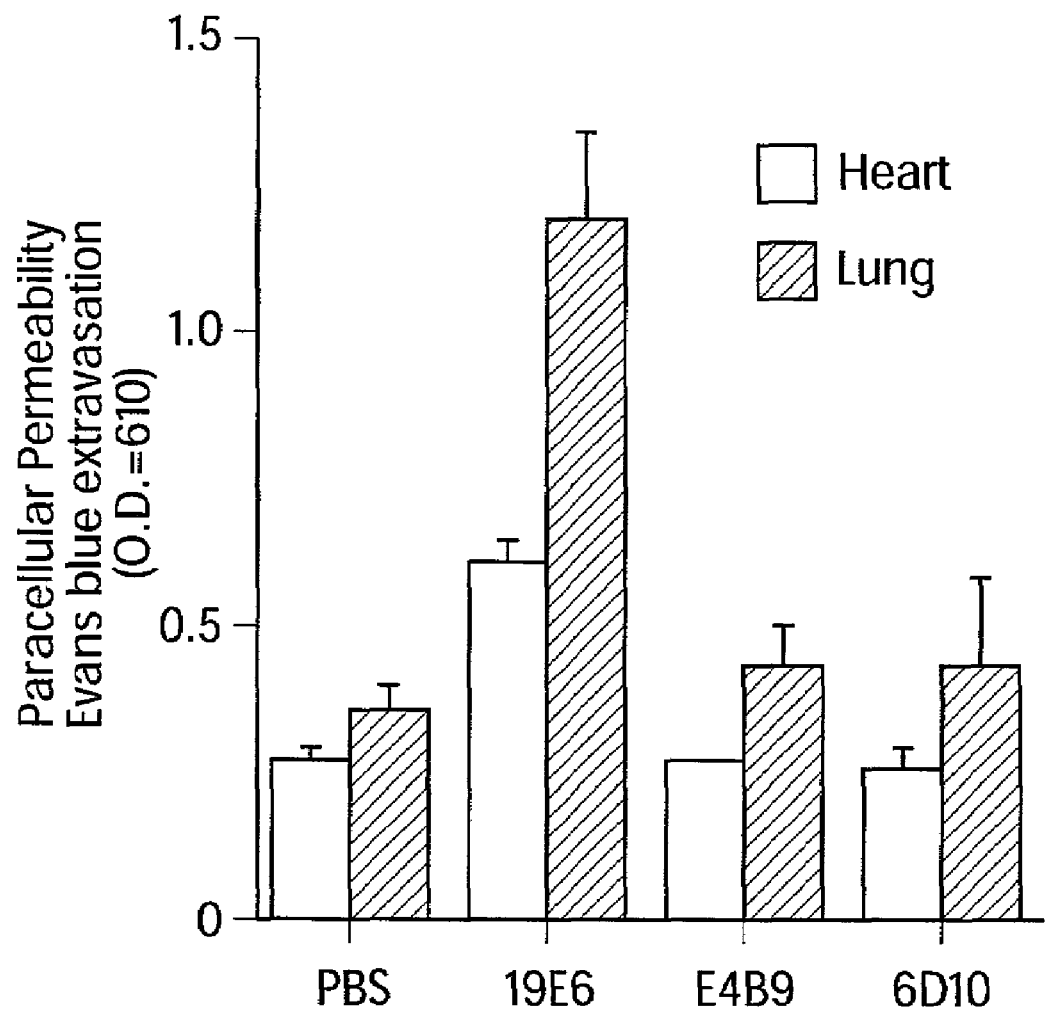

FIG. 4: Antibody E4B9 does not exhibit significant effect on paracellular permeability. Antibodies E4B9 and 6D 10 do not exert dramatic effect on vascular permeability.

Figure 5A:
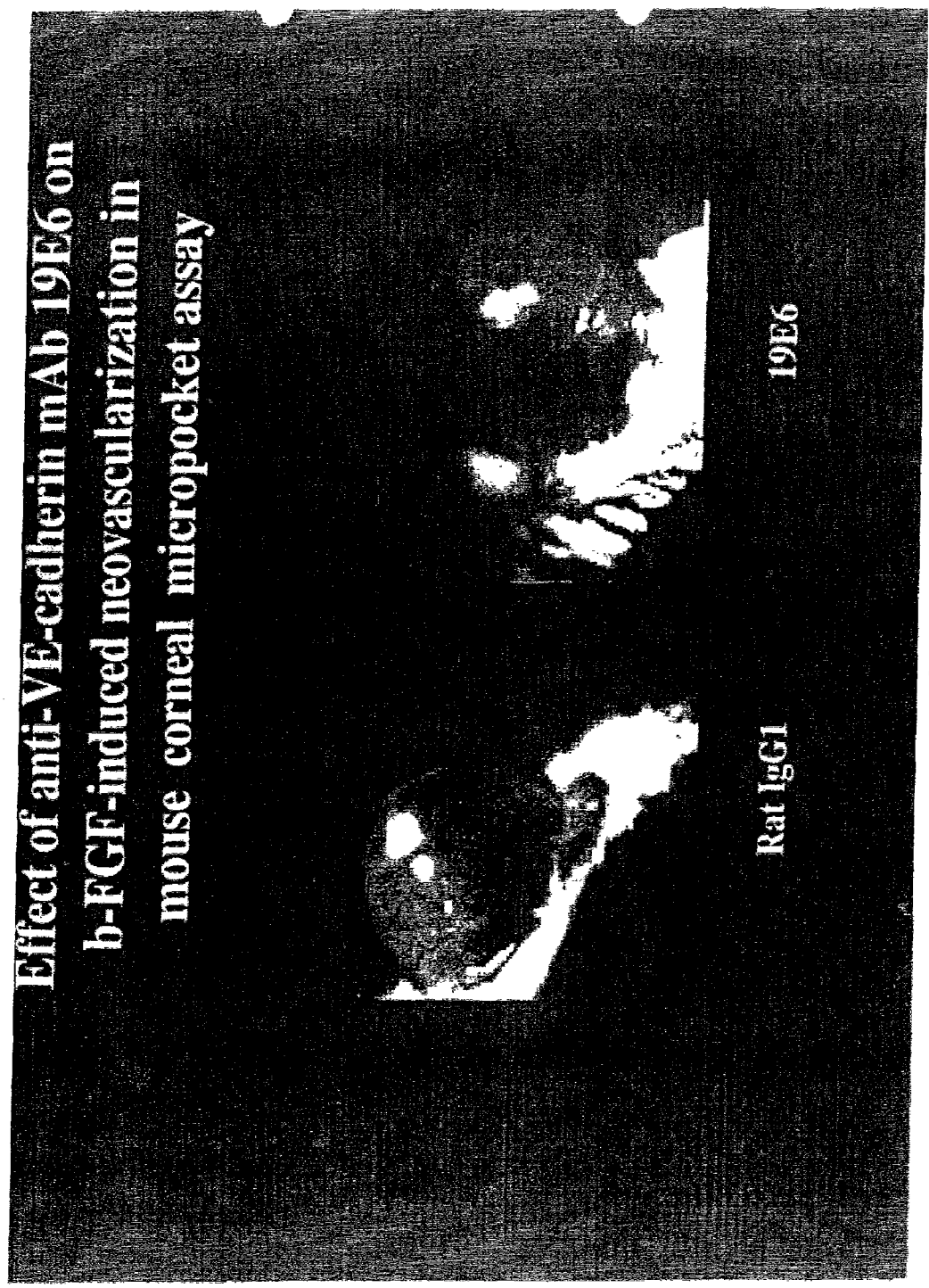
Figure 5B:
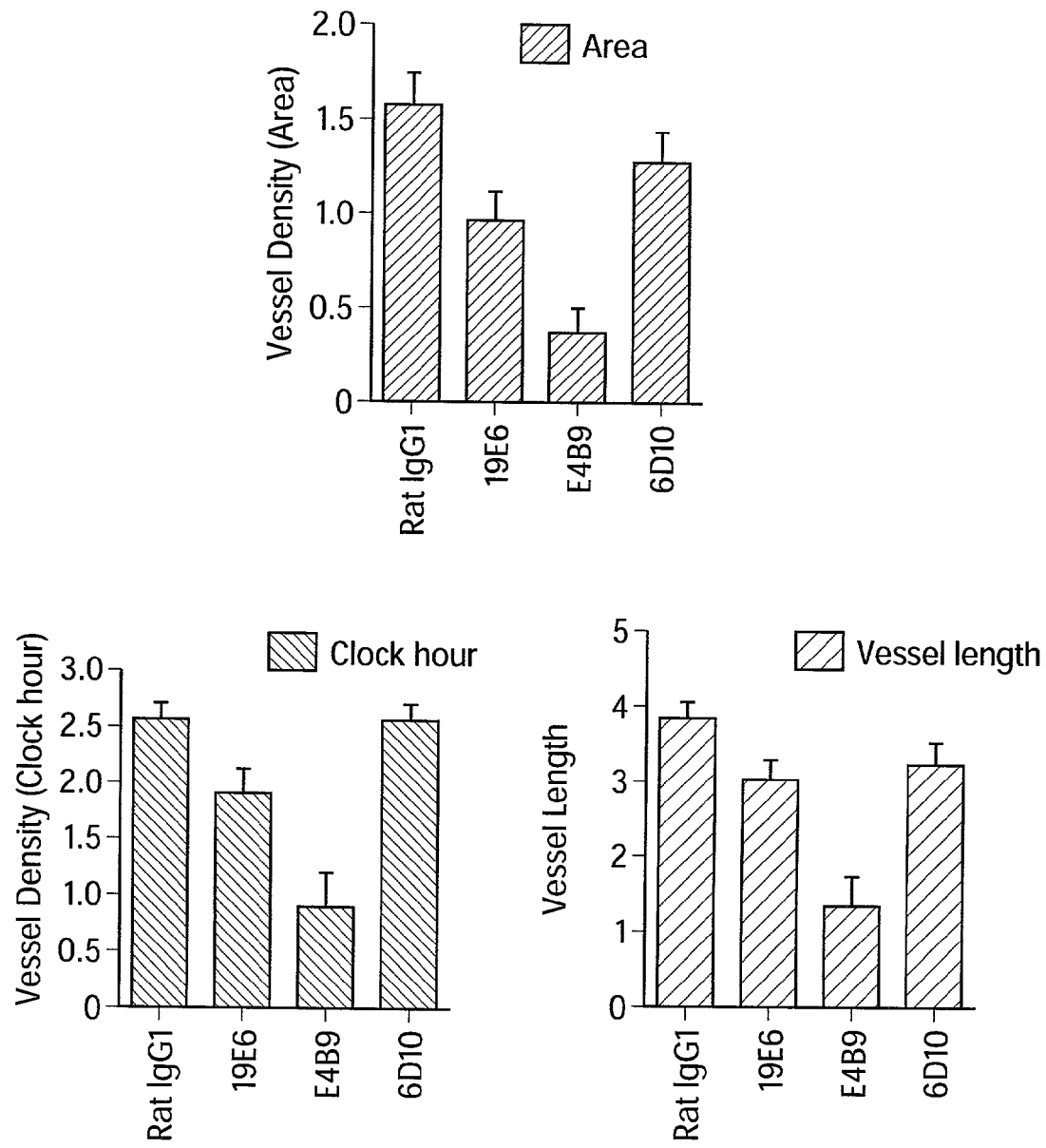

FIGS. 5A & 5B: Antibody E4B9 exhibits potent anti-angiogenesis activity in mouse corneal micropocket assay. Three representative eyes from each experimental group (6 mice/group) are tested. Antibody E4B9 possesses >80% inhibitory activity on corneal neovascularization.

Figure 6:
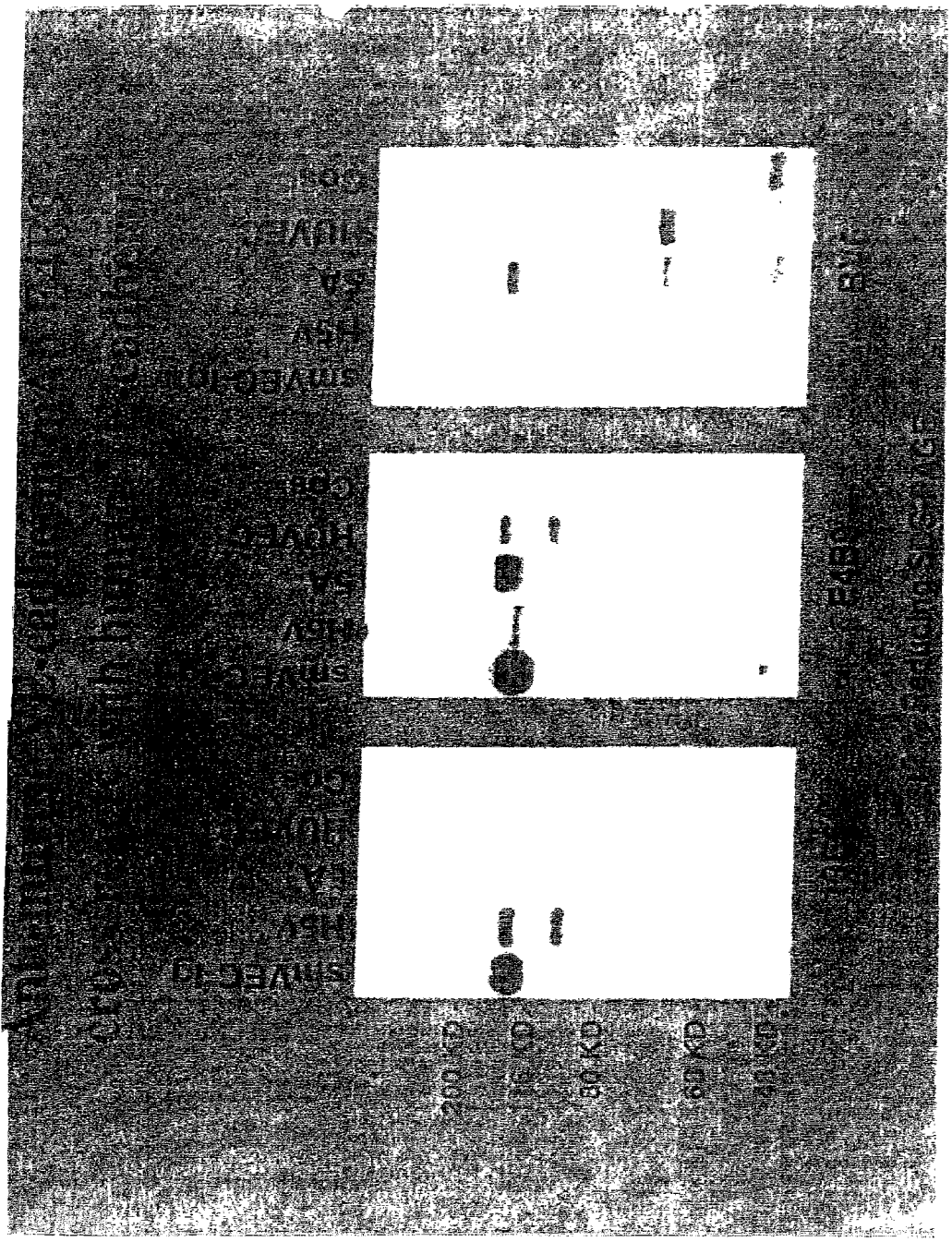

FIG. 6: Antibody E4B9 cross-reacts with human VE-cadherin.

Figure 7:
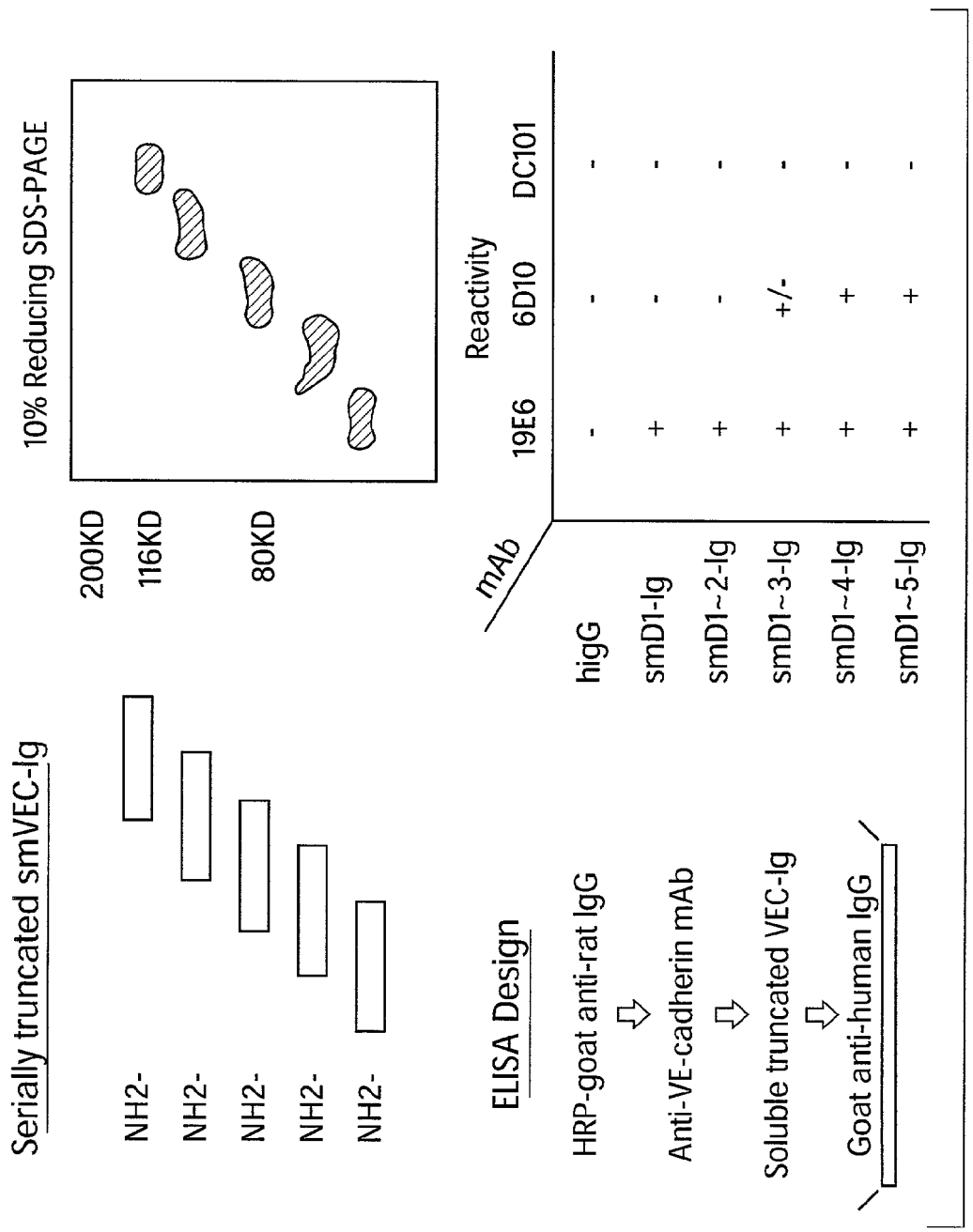

FIG. 7: Epitope mapping of new monoclonal antibodies. Strategy for mapping the epitope of m Ab 19E6 and 6D10.

Figures 8, 9:
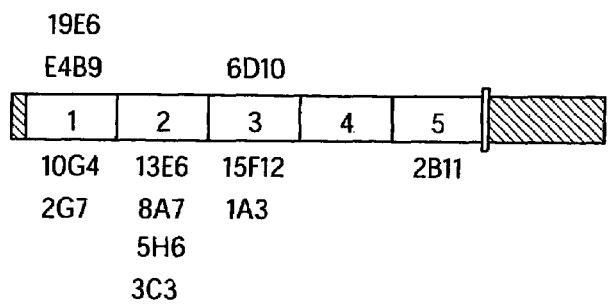

FIG. 8: Summary of the epitope information for anti-ECD1 peptide antibodies. Antibody 10G4 epitope was mapped to the domain 1 of mouse VE-cadherin using the same strategy as previously described in FIG. 7.

FIG. 9: Predicted epitope region for antibody 19E6 and 10G4. The underlined regions are the epitopes for antibodies E4B9 and Cad-5, respectively.

DETAILED DESCRIPTION OF THE INVENTION

The present invention provide antibody antagonists for VE-cadherin that inhibit VE-cadherin to VE-cadherin interactions without substantially disrupting already formed adherens junctions. In so doing, the antagonist substantially inhibits or prevents intercellular formation of new adherens junctions without substantially disrupting existing adherens junctions. Thus, these antibodies, and fragments thereof that retain the antigenic specificity of the intact antibody, are capable of specifically binding to a site on a mammalian VE-cadherin at the 15-20 N-terminal amino acids of domain 1 of the mammalian VE-cadherin, are capable of inhibiting VE-cadherin-mediated adherens junction formation in vitro but are not capable of exerting any significant or substantial effect on paracellular permeability in vitro. The binding site is preferably within the first 15 amino acids of the N-terminus of the VE-cadherin.

Alternatively, specific binding can be to a site on a mammalian VE-cadherin that is within the about 15 to about 20 N-terminal amino acids of domain 1 of a VE-cadherin wherein the N-terminal amino acids have an insertion, deletion or substitution of from 1 to about 5 amino acids relative to a VE-cadherin amino acid sequence. Likewise, specific binding can be to (1) a site with in the 15 N-terminal amino acids of any allelic variation of a VE-cadherin; (2) a peptide having an amino acid sequence of SEQ ID NO: 1 (DEIWNOMHIDEEKNE); a peptide having an amino acid sequence of SEQ ID NO: 2 (DWIWNOMHIDEEKNE); or a peptide having an amino acid sequence of SEQ ID NO: 3 (DWIWNQMHIDEEKNT). In all cases, the antibody antagonist retain the ability to inhibit formation of new junctions without disrupting existing junctions.

Hence the antibodies and antibody fragments of this invention do not exert any significant or substantial effect on vascular permeability in vivo. Similarly, the antibodies and antibody fragments of the invention are substantially non-toxic when administered to an animal or mammal. Likewise the antibodies and antibody fragments of the invention can inhibit angiogenesis in vivo or in vitro or inhibit tumor metastasis. The preferred antibody of the invention is murine monoclonal antibody E4B9.

Mammals of the invention include, but are not limited to, domesticated animals (such as cattle, pigs, dogs and cats), mice, primates and humans. Humans are the preferred mammal.

The antibodies and antibody fragments of the invention can be used to in methods of inhibiting angiogenesis; in methods of inhibiting tumor metastasis; in methods of treating a cell proliferative disorder associated with vascularization; and in methods for reducing or inhibiting tumor vasculature.

The present invention also includes chimeric, single chain, and humanized antibodies, as well as diabodies, triabodies, Fab fragments, or the product of an Fab expression library.

The antibodies of the invention can be prepared by conventional methods which are well know in the art. Preferably the antibodies are monoclonal antibodies but the invention also contemplates use of monospecific polyclonal antibodies. Monospecific polyclonal antibodies can be prepared by adsorbing out unwanted specificities from a preparation of polyclonal antibodies prepared with a suitable VE-cadherin immunogen. Immunogens suitable for preparation of the antibodies include but are not limited to a mammalian VE-cadherin, fragments of a mammalian VE-cadherin, preferably extracellular domains from VE-cadherin, peptides from the N-terminal domain 1 of a mammalian VE-cadherin, and fusion proteins with any of these molecules. Where appropriate the molecules (e.g., peptides) can be attached to carrier molecules such as BSA, KLH or any other carrier know in the art. The preferred immunogen is peptide consisting essentially of the 15 N-terminal amino acid residues of a mammalian VE-cadherin.

Techniques used for preparation of monoclonal antibodies, include but are not limited to, the hybridoma technique (Kohler & Milstein, *Nature*, 256:495-497 (1975)), phage display techniques, the trioma technique, the human B-cell hybridoma technique (Kozbor et al., *Immunology Today* 4:72, (1983)), and the EBV-hybridoma technique to produce human monoclonal antibodies (Cole, et al., 1985, *In Monoclonal Antibodies and Cancer Therapy*, Alan R. Liss, Inc., pp. 77-96).

Another aspect of the invention includes hybridomas which produce monoclonal antibodies of the present invention. One such hybridoma producing rat anti-murine VE-cadherin E4B9 has been deposited with the American Culture Collection (10801 University Blvd., Manassas, VA. 20110-2209 USA (ATCC) on Mar. 31, 2000, and has been assigned accession number PTA-1618.

Techniques described for the production of single chain antibodies (U.S. Pat. No. 4,946,778, incorporated herein by reference) are adapted to produce single chain antibodies to immunogenic polypeptide products of this invention.

For example the antibodies of the invention can be raised against VE-cadherin peptides, as well as fragments, analogs and derivatives of a VE-cadherin peptide. The terms protein, peptide, and polypeptide, are used interchangeably herein. The terms "fragment," "derivative" and "analog" refer to a polypeptide which either retains substantially the same biological function or activity as a VE-cadherin polypeptide, or retains the ability to bind the ligand even though the polypeptide does not function as a chemokine receptor, for example, a soluble form of the membrane polypeptide. The polypeptide of the present invention comprises, for example, a recombinant polypeptide, a natural polypeptide or a synthetic polypeptide.

An analog includes, for example, a proprotein which is activated by cleavage of the proprotein portion to produce an active mature polypeptide. Fragments of VE-cadherin polypeptide include VE-cadherin peptides having an N-terminal fragment comprising amino acid sequence of FIG. 2, or a fragment thereof. Derivatives or analogs of the polypeptide of FIG. 2, include one or more sequences of SEQ ID NOS 1-3, and comprise, for example, (i) peptides in which one or more of the amino acid residues are substituted with a conserved or non-conserved amino acid residue, (ii) peptides in which one or more of the amino acid residues include a substituent group, (iii) peptides in which the mature polypeptide is fused with another compound, such as a compound to increase the half-life of the polypeptide (for example, polyethylene glycol), (iv) peptides in which the additional amino acids are fused to the mature polypeptide for purification of the polypeptide(v) peptides in which a fragment of the polypeptide is soluble, i.e. not membrane bound, yet still binds ligands to the membrane bound peptide or receptor, or (vi)a combination of (i) to (v). Such fragments, derivatives and analogs are deemed to be within the scope of those skilled in the art from the teachings herein.

The polypeptides and polynucleotides of the present invention are preferably provided in an isolated form, and preferably are purified to homogeneity. However, this is not always necessary. Additionally, the polypeptides of the invention have at least 70% similarity (preferably a 70% identity) to one or more peptides of SEQ ID NOS. 1-3 and more preferably a 90% similarity (more preferably a 90% identity) to one or more peptides of SEQ ID NOS. 1-3 and still more preferably a 95% similarity to the peptides of SEQ ID NOS 1-3 and to portions of such peptide.

As known in the art "similarity" between two polypeptides is determined by comparing the amino acid sequence and conserved amino acid substitutes thereto of the polypeptide to the sequence of a second polypeptide.

According to another embodiment of the invention, the antibodies of the invention can be prepared by recombinant DNA techniques by cloning and expressing all or part of a known antibody. Using such techniques, which are known in the art, a humanized version of non-human antibodies can be prepared. for example a humanized version of monoclonal E4B9 can be readily prepared by cloning the gene encoding this antibody in to an appropriate expression vector. Useful the nucleic acids in this regard are those which encodes an amino acid sequence wherein the amino acid sequence comprises the variable region, hypervariable region, or both of a monoclonal antibody that specifically binds to domain 1 of an extracellular domain of a VE-cadherin peptide to inhibit new junction formation without disturbing normal vasculature.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred embodiment of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

The constructs in host cells are used in a conventional manner to produce the gene product encoded by the recombinant sequence. Appropriate cloning and expression vectors for use with prokaryotic and eukaryotic hosts are described by Sambrook, et al., *Molecular Cloning: A Laboratory Manual, Second Edition*, Cold Spring Harbor, N.Y, (1989).

According to another aspect of the invention, transgenic mammals are provided that express humanized antibodies to immunogenic polypeptide products of this invention. Novel transgenic mammalian hosts, other than primates, particularly other than human, are provided, where the host is capable of mounting an immune response to an immunogen, where the response produces antibodies having primate, particularly human, constant and/or variable regions or such other effector peptide sequences of interest.

The hosts are characterized by being capable of producing xenogenic or modified antibodies as a result of substitution and/or inactivation of the endogenous immunoglobulin subunit encoding loci. The modifications retain at least a portion of the constant region which provides for assembly of the variable region binding site bonded at the C-terminus to a functional peptide. The functional peptide takes many forms or conformations and serves, for example, as an enzyme, growth factor, binding protein, ligand, cytokine, effector protein, chelating proteins, etc. The antibodies are any isotype, i.e., IgA, IgD, IgE, IgG, IgM or subtypes within the isotype.

Transgenic hosts include murine, lagomorpha, ovine, porcine, equine, canine, feline, and the like. For the most part, mice have been used for the production of B-lymphocytes. It should be understood that other animals may be readily substituted for the mice, following the same procedures.

Humanized and chimeric antibodies are prepared according to the following strategies. In one strategy, the human heavy and light chain immunoglobulin gene complexes are introduced into the mouse germ line and in a separate step the corresponding mouse genes are rendered non-functional. Polynucleotides encoding human heavy and light chain are reconstructed in an appropriate eukaryotic or prokaryotic microorganism and the resulting polynucleotide fragments are then introduced into pronuclei of fertilized mouse oocytes or embryonic stem cells. Inactivation of the endogenous mouse immunoglobulin loci is achieved by targeted disruption of the appropriate loci by homologous recombination in mouse embryonic stem cells. In each case chimeric animals are generated which are derived in part from the modified embryonic stem cells and are capable of transmitting the genetic modifications through the germ line. The mating of mouse having a human immunoglobulin loci to mouse having an inactivated immunoglobulin loci yields animals that produce purely human antibody.

In another strategy, fragments of the human heavy and light chain immunoglobulin loci are used to directly replace the corresponding mouse loci by homologous recombination in mouse embryonic stem cells. This is followed by the generation of chimeric transgenic animals. The resulting human antibodies are isolated, for example, from other proteins by using an affinity column, having an Fc binding moiety, such as protein A, or the like.

The organization, relative location of exons encoding individual domains, and location of splice sites and transcriptional elements in a number of animals are known by those of ordinary skill in the art. In human, for example, the immunoglobulin heavy chain locus is located on chromosome 14. In the 5'-3' direction of transcription, the locus comprises a large cluster of variable region genes ($V_H$), the diversity (D) region genes, followed by the joining ($J_H$) region genes and the constant ($C_H$) gene cluster. The size of the locus is estimated to be about 2,500 kilobases (kb). During B-cell development, discontinuous gene segments from the germ line Ig H locus are juxtaposed by means of a physical rearrangement of the DNA.

Production of a functional heavy chain immunoglobulin polypeptide requires three discontinuous DNA segments, from the $V_H$, D, and $J_H$ regions, to be joined in a specific sequential fashion generating the functional units. Once these units are formed specific heavy chains are produced following transcription of the immunoglobulin locus. There are two loci for immunoglobulin light (Ig L)chains, the kappa locus on human chromosome 2 and the lambda locus on human chromosome 22. The structure of the Ig L loci is similar to that of the Ig H locus, except that the D region is not present.

The entire V region, or various fragments of the V region is used to produce a broad spectrum of high affinity antibodies. For example, a subset of the known V region genes of the human heavy and light chain Ig loci (Berman et al., EMBO J. 7: 727-738 (1988)) is used to produce transgenic hosts, which transgenic host are capable of mounting a strong immune response and provide high affinity antibodies.

Antibodies or antibody analog producing B-cells from the transgenic host are used, for example, for fusion to a mouse myeloid cell to produce hybridomas or immortalized by other conventional process, i.e., transfection with oncogenes. These immortalized cells are then grown, for example, in continuous culture or introduced into the peritoneum of a compatible host for production of ascites.

As discussed above, present invention also provides for the production of polyclonal human anti-serum or human monoclonal antibodies or antibody analogs provided they retain the activities of the antibodies of the invention. Epitope binding component of the present invention refers to proteins consisting of one or more polypeptides substantially encoded by genes of the immunoglobulin superfamily (i.e., The Immunoglobulin Gene Superfamily, Williams & Barclay In: Immunoglobulin Genes, Honjo, Alt, and Rabbitts, eds., (1989) incorporated herein by reference). For example, an epitope binding component comprises part or all of a heavy chain, part or all of a light chain, or both. However, an epitope binding component must contain a sufficient portion of an immunoglobulin superfamily gene product to retain the ability to bind to a specific target, or epitope.

Included within the scope of this invention is bispecific antibodies that are formed by joining two epitope binding components that have different binding specificities.

It is well known that native forms of "mature" immunoglobulins vary somewhat in terms of length by deletions, substitutions, insertions or additions of one or more amino acids in the sequences. Thus, both the variable and constant regions are subject to substantial natural modification, yet are "substantially identical" and still capable of retaining their respective activities.

Polynucleotides encoding human constant and variable regions are isolated in accordance with well known procedures from a variety of human cells, but preferably immortalized B-cells. Similar methods are used to isolate non-human immunoglobulin sequences from non-human sources. Suitable source cells for the polynucleotides and their expressed and secreted products are obtained from a number of sources, such as the American Type Culture Collection ("Catalogue of Cell Lines and Hybridomas," Fifth edition (1985) Rockville, Md., U.S.A.) In addition to these naturally-occurring forms of immunoglobulin chains, "substantially identical" modified heavy and light chains are readily designed and manufactured utilizing various recombinant DNA techniques well known to those skilled in the art. For example, the chains vary from the naturally-occurring sequence at the primary structure level by several amino acid substitutions, terminal and intermediate additions and deletions, and the like. Alternatively, polypeptide fragments comprising only a portion of the primary structure are produced, which fragments possess one or more immunoglobulin activities (i.e., binding activity).

In particular, it is noted that like many genes, the immunoglobulin-related genes contain separate functional regions, each having one or more distinct biological activities. In general, modifications of the genes encoding the desired epitope binding components are readily accomplished by a variety of well-known techniques, such as site-directed mutagenesis (see, Gillman & Smith, Gene 8:81-97 (1979) and Roberts, et. al., Nature 328:731-734 (1987), both of which are incorporated herein by reference).

In preferred embodiments of the invention, the epitope binding component of the antibody of this invention is encoded by immunoglobulin genes that are "chimeric" or "humanized" (see, generally, Queen (1991) Nature 351:501, which is incorporated herein by reference). Once expressed, VE-cadherin antibodies, epitope binding components, their dimers, or individual light and heavy chains are purified according to standard procedures of the art, for example, ammonium sulfate precipitation, fraction column chromatography, gel electrophoresis and the like (see, generally, Scopes, Protein Purification, Springer-Verlag, N.Y. (1982)). Once purified, partially or to homogeneity as desired, the antibodies and fragments thereof are then used ,for example, therapeutically, diagnostically, in drug screening techniques, or in developing and performing assay procedures, such as immunofluorescent stainings, and the like.

Once a candidate anti-VE-cadherin monoclonal antibody is tested and confirmed to have no increase in vascular permeability in vivo, the in vivo activity and/or efficacy of the antibodies and antibody fragments can be determined by a number of methods know to those of skill in the art. Such assays include, but are not limited to, in vivo angiogenesis assays. Three in vivo angiogenesis assays, the corneal micropocket, the Matrigel plug and Alginate-encapsulated tumor cell assays are particularly useful to assess anti-angiogenic activity of VE-cadherin monoclonal antibodies. Typically, antibodies (or antibody fragments) are first tested in the corneal micropocket assay, since this assay requires less antibody for testing and is less time-consuming than the other assays. Various amounts of antibodies are either incorporated into surgically implanted pellets or administered in a systemic manner. Those antibodies with significant inhibitory activity on corneal neovascularization are further tested in the Matrigel plug and Alginate assays. The Matrigel plug and Alginate assays serve to confirm anti-angiogenic activities of anti-VE-cadherin antibodies and allow for quantification of anti-angiogenic activity between various antibodies and controls. Anti-VE-cadherin antibodies that show inhibition of angiogenesis in vivo are further tested for their anti-tumor activity in tumor models. A human A431 epidermoid carcinoma xenograft model, the Lewis lung subcutaneous tumor model and the Lewis lung metastasis model are used for these studies.

Example 5 provides additional assays as well as detailed examples applying such assays and techniques for further evaluating the antibodies and/or antibody fragments of the invention.

Pharmaceutical compositions comprising the antibody antagonists of present invention are useful for administration to subjects in subjects in need thereof. Administration is achieved by different routes of administration, including oral, or parenteral (subcutaneously, intramuscularly or intravenously.) The compositions for parenteral administration commonly comprise a solution of the antibody or a cocktail thereof dissolved in an acceptable carrier, preferably an aqueous carrier. A variety of aqueous carriers are used, i.e., water, buffered water, 0.4% saline, 0.3% glycine and the like. These solutions are sterile and generally free of particulate matter. These compositions are sterilized, for example, by conventional, well known sterilization techniques.

The carrier or diluent of the composition of invention comprises, for example, pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the agent in these formulations vary widely, i.e., from less than about 0.01%, preferably at least about 0.1% to as much as about 5% by weight. The concentration range is selected primarily based on fluid volumes, viscosities, or particular mode of administration selected.

Thus, a typical pharmaceutical composition for intramuscular injection is made up to contain, for example, about 1 ml sterile buffered water, and about 1 mg of the agent. A typical composition for intravenous infusion is made up to contain, for example, about 250 ml of sterile Ringer's solution, and 10 mg of the agent. Actual methods for preparing parenterally administrable compositions are known or apparent to those skilled in the art and are described in more detail in, for example, In: Remington's Pharmaceutical Science, 15th Ed., Mack Publishing Company (1980) which is incorporated herein by reference.

The antibodies of this invention are, for example, lyophilized for storage and reconstituted in a suitable carrier prior to use. This technique has been shown to be effective using conventional immunoglobulins and art-known lyophilization and reconstitution techniques. The compositions containing the present antibodies or a cocktail thereof are administered for prophylactic and/or therapeutic treatments.

In accordance with the invention, a method of inhibiting angiogenesis comprises administering a composition containing an antibody or antibody fragment of the invention to a mammal for a time and in an amount effective to inhibit angiogenesis. Similarly, the antibodies and antibody fragments can be used in methods of inhibiting tumor metastasis in a mammal by administering a composition containing an antibody of the invention to a mammal for a time and in an amount effective to inhibit metastasis of a tumor.

In one embodiment, the invention provides a method of treating a cell proliferative disorder associated with vascularization in a mammal which comprises administering a the composition containing an antibody or antibody fragment to a mammal in an amount effective to inhibit proliferation of endothelial cells without disturbing the normal vasculature.

Another embodiment relates to a method for reducing or inhibiting tumor vasculature in a mammal which comprises administering a composition containing an antibody or antibody fragment to a mammal in an amount effective to inhibit blood vessel formation without adversely affecting existing vasculature. The tumors that can be treated in accordance with the invention, include but are not limited to, carcinomas, gliomas, sarcomas, adenocarcinomas, adenosarcomas, adenomas as well as liquid tumors such as leukemic and lymphoid tumors. These tumors can occur in all parts of the body, for example, in the brain, breast, lung, colon, kidney, bladder, head and neck, ovary, prostate, pancreas, skin, bone, bone marrow, blood, thymus, uterus, testicles, cervix, and liver.

As used herein "Cell proliferative disorders" refer to disorders wherein unwanted cell proliferation of one or more subset of cells in a multicellular organism occurs resulting in harm (i.e., discomfort or decreased life expectancy) to the multicellular organism. Cell proliferative disorders occur in different types of animals and in humans, and include blood vessel proliferative disorders, fibrotic disorders, angiogenesis, tumor growth, rheumatoid arthritis, and age-related muscular degeneration.

In another embodiment, the invention provides a method of gene therapy which comprises administering a nucleic acid of encoding an antibody or antibody fragment of the invention to a mammal in an amount and for a time effective to inhibit angiogenesis at a predetermined site or to inhibit tumor neovascularization. Methods of gene therapy are known in the art. This method is applicable to treating the diseases associated with angiogenesis as mentioned herein as well as for inhibiting the tumors listed above.

Therapeutic applications according to the invention, comprise treatment, prevention and amelioration. If treatment is intended, the composition is administered to a patient already affected by the particular disease, in an amount sufficient to cure or at least partially arrest the condition and its complications. An amount adequate to accomplish this is defined as a "therapeutically effective dose." Amounts effective for this use depends upon the severity of the condition and the general state of the patient's own immune system, but generally range from about 0.01 to about 100 mg of the antibody or antibody fragment per dose, with dosages of from about 1 to about 10 mg per patient being more commonly used.

In prophylactic applications, compositions containing the antibody antagonist, or a cocktail thereof if beneficial, is administered to a patient not already in a disease state to enhance the patient's resistance. Such an amount is defined to be a "prophylactically effective dose." In this use, the precise amount again depends upon the patient's state of health and general level of immunity, but generally ranges from about 0.1 to 100 mg per dose, preferably from about 1 to about 10 mg per patient. Single or multiple administrations of the compositions are carried out with dose levels and pattern being selected by the treating physician. In any event, the pharmaceutical formulations should provide a quantity of the agent of this invention sufficient to effectively treat the patient.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed in an exemplary embodiment may be made by one skilled in the art and it is intended that such modifications, changes, and substitutions are to be included within the scope of the present invention.

EXAMPLE 1

Methods

Monoclonal Antibody Preparation: Lewis rats (6-8 week old females) were injected subcutaneously (s.c.) with 0.1 ml of protein or peptide mixed in Freund's complete adjuvant using a 25-gauge needle. Rats were boosted every 2-3 weeks with antigen and bled via the tail vein every week. After 3 booster immunizations or when sera titers reach maximal levels, mice were sacrificed by $CO_2$ inhalation. Spleens were recovered from sacrificed animals for monoclonal antibody generation by conventional techniques.

Antibody Screening: Hybridoma supernatants were screened in by an enzyme-linked immunosorbent assay (ELISA) to identify antibodies which bound to VE-cadherin.

Junction Formation/Ca Switch Assay: The junction formation assay was developed based on a modification of the calcium switch assay (Gumbiner, B., & Simons, K., Cell Biol. 102:457468 (1986)). Transfectant CHO cells or endothelial cells expressing VE-cadherin are plated onto glass slides and allowed to form a confluent monolayer. The adherens junctions of the monolayer are artificially disrupted by depleting calcium from the culture medium by incubation with 5 mM EGTA for 30 min. EGTA-containing media is then removed and fresh media containing calcium is added to the culture to allow for formation of adherens junctions. The inhibition of junction formation is measured by addition of various concentrations of anti-VE-cadherin monoclonal antibody at the time calcium-containing fresh media is added. The kinetics of junction disruption and junction reformation processes correlate with the disappearance and reappearance of VE-cadherin in the adherens junctions. The formation of adherens junctions is visualized by immunofluorescent staining with a polyclonal antibody specific for mouse or human VE-cadherin. Immunostaining on another junctional adhesion molecule (CD31) is routinely included to ensure that the treated cell monolayer does not retract.

Paracellular Permeability Assay: The cell permeability assay is performed by seeding VE-cadherin-expressing CHO cell transfectants or endothelial cells in the top chamber of Costar transwells. Cultures are incubated for 2 days to allow for formation of adherens junctions and a confluent cell monolayer. Test antibodies are then added to the top chamber of cells along with FITC-dextran. The anti-VE-cadherin antibody effect on cell permeability (junction disruption) is measured as a function of FITC-dextran that permeates into the bottom chamber.

The permeability assay can be adapted to a format useful for early screening of monoclonal antibodies expressed in hybridoma culture supernatants. In brief, hybridoma cells are seeded into the bottom chambers of transwells (Costar, 6.0 mm diameter/0.3 um pore size) and co-cultured with a monolayer of cells expressing mouse VE-cadherin on the top filter. Cells used in this assay are either transfected CHO cells expressing the full-length mouse VE-cadherin molecule or the mouse H5V endothelioma cell line. After co-culture for 3-5 days, FITC-dextran (1 mg/ml) are added to the top chamber and permeability measured by fluorimetry as a function of FITC-dextran that crosses the cell monolayer into the bottom chamber. Permeability activity (junction disruption) of candidate monoclonal antibody are calculated as the percentage of increase in permeability of VE-cadherin expressing cells as compared to control wells containing an unrelated control rat monoclonal antibody. Permeability activity are normalized by hybridoma cell counts and total rat IG production to control for variation in growth rate and antibody production between different hybridoma clones. The junction disrupting activity of the new monoclonal antibody are compared to that of the monoclonal antibody 19E6, which is known to have high junction disrupting activity (>150% increase in permeability). Only those antibodies that exhibit no disruption (approx. 25% increase in permeability) or modest disruption (approx. 25-75% increase in permeability) activity are subjected to further screening for their junction inhibiting activity in the junction formation assay.

Corneal Pocket Assay: C57/BL mice (6-8 week old female) were anesthetized with ketamine and a corneal pocket was created in both eyes using a von Graefe cataract knife. Hydron pellets containing basic-FGF with or without test antibody at various doses were then implanted into each eye pocket. Alternatively, hydron pellets containing basic-FGF were implanted and mice treated by i.p. injection with a 25-gauge needle of test antibody at various doses or controls every 3 days. After 6-7 days, the angiogenic response was examined by slit-lamp biomicroscopy and photographed. Mice were sacrificed by $CO_2$ inhalation and the eyes excised and prepared for further histological analysis.

EXAMPLE 2

VE-Cadherin Monoclonal Antibodies that Inhibit Adherens Junction Formation without Disrupting Existing Junctions Two groups of Lewis rats were immunized with either a mixture of four KLH-coupled peptides having sequences from the N-terminal domain 1 of murine VE-cadherin (FIG. 2) or with affinity-purified soluble mouse VE-cadherin (sm-VEC-Ig) which had been expressed in CHO cells. This immunogen encompasses the entire extracellular region of mouse VE-cadherin fused to human Fc chain. The resulting hybridoma clones were tested for production of antibodies with binding activity to VE-cadherin using a conventional ELISA format. This screening identified twenty (20) rat anti-murine VE-cadherin antibodies, 10 from each of the originally immunized groups of rats.

Several properties of these monoclonal antibodies were examined and the results are summarized in Tables 1 and 2.

The 20 candidate VE-cadherin antibodies were tested in the "calcium-switch" and "permeability" assays to examine their new junction formation inhibiting activity and existing junction disrupting activity, respectively. Among these 20 antibodies, E4B9 was shown to specifically inhibit adherens junction formation without adversely affecting normal vasculature (FIGS. 3 and 4). Furthermore, the E4B9 antibody was also tested in an in vivo angiogenesis assay and showed greater than 80% inhibition of corneal neovascularization (FIG. 5). While another antibody (19E6) was also identified as a potent inhibitor of VE-cadherin-mediated adherens junction formation by the in vitro assay criteria, this antibody disrupts existing junctions (FIG. 3). The key biological activities of these two antibodies are summarized in Table 3 along with data from other murine and human anti-VE-cadherin antibodies.

TABLE 1

Anti-VE-Cadherin Antibodies Prepared Against Peptide Immunogens

| MAb[1] | Bacterial mECD1~2 (Blot) | Native VEC (Blot) | $Ca^{2+}$-switch Assay (IF) | Paracellular Permeability (% Increase) |
|---|---|---|---|---|
| 19E6[2] | + | + | + | 120~50 |
| 6D10 | + | + | + | 20 |
| E4B9 (P1)[3] | + | + | + | <20 |
| E4G10 (P1) | + | + | + | <20 |
| E3F2 (P2) | + | − | − | <20 |
| 1F6.1 (P2) | + | − | − | <20 |
| 10E4.1 (P2) | + | + | − | <20 |
| 8D6.1 (P4) | + | + | − | <20 |
| 9C6.1 (p4) | + | − | − | <20 |
| 3F7.1 (p4) | + | + | − | <20 |
| 4F1.1 Sup (mED1~2) | + | + | − | <20 |

[1]Abbreviations: MAb, monoclonal antibody; bacterial mECD1~2, bacterially-expressed protein containing extracellular domains 1 and 2 of the N-terminus of murine VE-cadherin; IF, immunofluorescence.
[2]Control antibody.
[3]This antibody, E4B9, cross-reacts with human VE-cadherin.

TABLE 2

Anti-VE-Cadherin Antibodies Prepared Against sm VEC-Ig

| MAb[1] | ELISA | ?? (Blot) | $Ca^{2+}$-switch Assay (IF) | Paracellular Permeability | Domain |
|---|---|---|---|---|---|
| 10G4 | +++ | + | + | + | 1 |
| 9D9 | + | − | − | − | 1 |
| 2G7 | + | − | − | − | 1 |
| 13E6 | +++ | + | − | − | 2 |
| 8A7 | +++ | + | − | − | 2 |
| 5H6 | ++ | + | − | − | 2 |
| 3C3 | + | − | − | − | 2 |
| 15F12 | +++ | + | − | − | 2 |
| 1A3 | + | − | − | − | 2~3 |
| 2B11 | +++ | + | − | − | 5 |

[1]See Table 1.

TABLE 3

| MAb[1] | Epitope | Junction disruption vs. Junction inhibition (Permeability Ca2+-switch) | |
|---|---|---|---|
| Anti-human VEC | | | |
| Cad5 | Domain 1 | +++ | +++ |
| BV9 | Domain 3 | +++ | +++ |
| BV6 | Domain 3 | +++ | +++ |
| TEA | Domain 4 | +/− | +/− |
| Hec1.2 | Domain 4 | − | − |

| | | | | Toxicity |
|---|---|---|---|---|
| Anti-murine VEC | | | | |
| 19E6 | Domain 1 | +++ | +++ | + |
| E4B9 | Domain 1 | +/− | +++ | − |
| 10G4 | Domain 1 | ND | +++ | ND |
| 6D10 | Domain 3-4 | +/− | +/− | − |

[1]See Table 1.

EXAMPLE 3

E4B9 Crossreacts with Human VE-Cadherin

The murine epitope sequence recognized by antibody E4B9 shares 100% homology with human VE-cadherin, so this antibody was examined to determine if it cross-reacts with human VE-cadherin. Western-blot analysis of several VE-cadherin expressing human and murine cell indicated that E4B9 indeed cross-reacts with human VE-cadherin (FIG. 6). This finding facilitates development of a "humanized" E4B9 antibody and its success in the preclinical development since its anti-tumor activity can be tested extensively in several mouse models.

EXAMPLE 4

Epitope Mapping

To define the specific VE-cadherin domain targeted by each new monoclonal antibody, a series of smVE-cadherin-Ig truncations were recombinantly generated. The epitope mapping strategy is shown in FIG. 7. The culture supernatants from COS cells transfected with these smVE-cadherin-Ig truncation-bearing plasmids were used with ELISA to determine the epitope domains for each monoclonal antibody. Fine epitope mapping of the three functional blocking monoclonal antibodies (E4B9, 19E6 and 10G4) were made. The preliminary results showed that 19E6 and 10G4 recognize regions different from that of monoclonal antibody E4B9 (FIGS. 7-9).

Antibody E4B9 inhibits new junction formation without disrupting existing junctions whereas other antibodies (19E6, 10G4 and Cad-5) disrupt existing junctions. During the later stage of angiogenesis, detached endothelial cells have to assemble into a capillary-like tubular structures that is mediated by the homophilic adhesion of VE-cadherin molecules, presumably from the same cells (strand dimers) first and then from the opposing cells (adhesion dimers). Therefore, an antibody (such as E4B9) that antagonizes the "strand dimer" formation is sufficient to inhibit new junction formation. In contrast, disruption of the existing junctions is a reversed process, i.e., from "adhesion dimers" to "strand dimers". Those antibody antagonists that are specific to the "adhesion dimers" thus appear more disruptive to the existing vasculature. Evidence supporting this model is provided by fine epitope mapping and a crystal structure of VE-cadherin.

EXAMPLE 5

Miscellaneous In Vivo Assessments

Vascular permeability in tissues are analyzed by a Miles' type assay with some modifications (Corda, et al., *Proc. Natl. Acad. Sci.* 96:9815-9820 (1999) incorporated herein by reference. In brief, the test antibody or fragment is administered either intraperitoneally or intravenously to mice at various doses (50-1000 μg/dose). Increased vascular permeability is determined by injecting Evans blue dye (100 micro liter of 1 mg/ml) intravenously at various times (6 h, 12 h, 24 h and 48 h.) Following administration, typically 20 minutes later, mice are anesthetized by ketamine and perfused with approximately 20 ml of PBS. Mouse organs are removed and homogenized in TCA/ethanol (1:1 v/v). The Evans blue content in the tissue homogenates are quantified by spectrophotometry (OD=510 nm). The antibody effect on vascular permeability is measured as the percentage increase in Evans blue dye compared to control antibody.

Anti-mouse VE-cadherin monclonal antibodies are evaluated for their anti-tumor effects in the Lewis lung subcutaneous primary tumor model, the Lewis lung metastasis model and the human epidermoid (A431) subcutaneous xenograft model. Primary subcutaneous Lewis lung tumors are established in C57BL/6 mice (6-8 week old females) by s.c. injection of 1×10$^5$ tumor cells in a suspension of Hanks balanced salt solution into the right flank using a 22-gauge needle. Mice (10 mice/group) are treated with VE-cadherin antibody (50-1000 µg) or an unrelated control rat IgG every 3-4 days for 3-4 weeks or until the mice become moribund. Tumor volume is measured twice weekly using calipers and the volume calculated using the formula $-\pi/6\times\text{diameter}^2$. Tumors from mice in each treatment group are removed surgically for histology and stained with anti-CD31 antibody to assess vascular density. In the Lewis lung metastasis model, primary tumors are established in the footpads of C57BL/6 mice. After 28 days, when the tumors reach approximately 100 mm$^3$, the primary tumor is removed and 24 h later mice (10 mice/group) are administered i.p. with VE-cadherin antibody (50-1000 µg) or an irrelevant control rat IgG every 3 days. After 4 weeks of treatment, mice are sacrificed and lungs examined for tumor metastasis. Lungs are also examined by histology for evidence of micrometastases and stained with anti-CD31 antibody to assess vascular density.

The human epidermoid carcinoma cell line A431 is injected subcutaneously into the right flank of a thymic mice. Once tumors reach 150 mm$^3$, mice are divided randomly into treatment groups (10 mice/group) and administered VE-cadherin antibody (50-1000 µg) or an unrelated control rat IgG every 3 days for 4 weeks. Tumors are measured twice weekly and removed after mice become moribund or at 4 weeks. Tumors are also examined by histology and stained with anti-CD31 antibody to assess vascular density. Evaluation of the VE-cadherin therapy is based on tumor growth rate, tumor regression and histological evaluation of neovascularization of tumors. The activity of the antibody in each tumor model are compared to 19E6 monoclonal which serves as a positive control. The negative control is an unrelated rat monoclonal antibody. Statistical analysis of tumor growth are determined using a two-tailed Student's T-test where a p value of <0.05 is considered significant.

In Matrigel Plug Assay C57/BL mice (6-8 week old female) are injected s.c. with 0.5 ml of angiogenic factors mixed in Matrigel using a 25-gauge needle. Mice are then ;treated by i.p. injection with a 25-gauge needle with various doses of VE-cadherin antibodies or controls every 3 days. After 10 days mice are sacrificed by CO2 inhalation and the plugs recovered from the animals for further histological analysis.

In Agitate Encapsulated Tumor Cell Assay C57BL/6 mice (6-8 week old female) are anesthetized with ketamine and then 4 beads surgically implanted s.c. into the upper third of the back and pushed away from the incision site. The incision is closed with surgical clips. Mice are then treated by i.p. injection with a 25-gauge needle with various doses of VE-cadherin antibodies or controls every 3 days. After 12 days, mice are injected i.v. with 100 µl of a 100 mg/kg FITC-Dextran solution (MW-150,000). Animals are sacrificed by $CO_2$ inhalation and beads are removed, kept in the dark and processed for FITC quantitation.

In Human Tumor Xenograft Model, athymic nude (nu/nu) mice (6-8 week old female) are injected s.c. with 2×106 A431 human epidermoid tumor cells in a suspension of Hanks balanced salt solution into the right flank with a 22-gauge needle. Once tumors reach 100-200 mm$^3$ in size, VE-cadherin antibodies or a control antibody is administered to mice twice weekly by i.p. injection with a 25-gauge needle for 6 weeks or until mice become moribund. Tumor volumes are measured twice weekly with calipers. Animals which become tumor free during the study are followed for up to 8 weeks after the completion of treatment. Mice which complete the study or become moribund are then sacrificed by $CO_2$ inhalation.

We claim:

1. An isolated monoclonal antibody or an isolated fragment thereof capable of specifically binding to a site on a mouse or human VE-cadherin, said site being within the about first 15 N-terminal amino acids of domain 1 of the VE-cadherin, wherein said antibody or fragment thereof is capable of inhibiting VE-cadherin mediated adherens junction formation in vitro but does not exert any significant or substantial effect on paracellular permeability in vitro.

2. The monoclonal antibody or fragment thereof of claim 1, wherein said monoclonal antibody or fragment thereof does not exert any significant or substantial effect on vascular permeability in vitro.

3. The monoclonal antibody or fragment thereof of claim 1, wherein said monoclonal antibody or fragment thereof is substantially non-toxic when administered to an animal or mammal.

4. The monoclonal antibody or fragment thereof of claim 1, wherein said monoclonal antibody or fragment thereof inhibits angiogenesis in vivo or in vitro or inhibits minor metastasis.

5. The monoclonal antibody or fragment thereof of claim 1, wherein said monoclonal antibody or fragment thereof inhibits formation of new adherens junctions without disturbing existing adherens junctions.

6. The monoclonal antibody or fragment thereof of claim 1, wherein said monoclonal antibody is murine monoclonal antibody E4B9 of ATCC accession number PTA-1618.

7. A hybridoma which produces the monoclonal antibody of claim 1.

8. A hybridoma ATCC of Accession No. PTA-1618 which produces the monoclonal antibody of claim 7.

9. The monoclonal antibody or fragment thereof of claim 1, wherein said monoclonal antibody or fragment thereof is a single chain antibody, is humanized, is chimerized or is bispecific.

10. The monoclonal antibody or fragment thereof of claim 1, wherein said monoclonal antibody or fragment thereof is fused to a heterologous polypeptide.

11. A pharmaceutical composition comprising the monoclonal antibody or fragment thereof of any one of claims 1-6, and 9-10 and a pharmaceutically acceptable carrier or diluent.

* * * * *

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Asp Glu Ile Trp Asn Gln Met His Ile Asp Glu Glu Lys Asn Glu
 1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Asp Trp Ile Trp Asn Gln Met His Ile Asp Glu Glu Lys Asn Glu
 1               5                   10                  15
```

```
<210> SEQ ID NO 3
<211> LENGTH: 15
<212> TYPE: PRT
<213> ORGANISM: Artificial Sequence
<220> FEATURE:
<223> OTHER INFORMATION: synthetic peptide

<400> SEQUENCE: 3

Asp Trp Ile Trp Asn Gln Met His Ile Asp Glu Glu Lys Asn Thr
 1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic peptide

<400> SEQUENCE: 4

Tyr Val Lys Asp Gln Ser Asn Tyr Asn Arg Gln Asn Ala Lys Tyr Cys
 1               5                  10                  15

<210> SEQ ID NO 5
<211> LENGTH: 18
<212> TYPE: PRT
<213> ORGANISM: Artificial Sequence
<220> FEATURE:
<223> OTHER INFORMATION: synthetic peptide

<400> SEQUENCE: 5

Lys Tyr Val Leu Gln Gly Glu Phe Ala Gly Lys Ile Phe Gly Val Asp
 1               5                  10                  15

Ala Cys
     18

<210> SEQ ID NO 6
<211> LENGTH: 15
<212> TYPE: PRT
<213> ORGANISM: Artificial Sequence
<220> FEATURE:
<223> OTHER INFORMATION: synthetic peptide

<400> SEQUENCE: 6

Leu Ile Val Asp Lys Asn Thr Asn Lys Asn Leu Glu Gln Pro Cys
 1               5                  10                  15
```